United States Patent
Menegan et al.

(12)

(10) Patent No.: US 9,561,175 B1
(45) Date of Patent: Feb. 7, 2017

(54) DEODORANT HEALTH SYSTEMS

(71) Applicants: Peter Menegan, Middletown, NY (US); Stephen Catanzaro, Middletown, NY (US)

(72) Inventors: Peter Menegan, Middletown, NY (US); Stephen Catanzaro, Middletown, NY (US)

(73) Assignee: Pete D. Menegan, Middletown, NY (US)

(*) Notice: Subject to any disclaimer, the term of this patent is extended or adjusted under 35 U.S.C. 154(b) by 158 days.

(21) Appl. No.: 14/602,116

(22) Filed: Jan. 21, 2015

Related U.S. Application Data (60) Provisional application No. 61/930,067, filed on Jan. 22, 2014.

(51) Int. Cl.
| | |
|---|---|
| *A61K 9/00* | (2006.01) |
| *A61Q 15/00* | (2006.01) |
| *A61K 8/02* | (2006.01) |
| *A61K 8/96* | (2006.01) |
| *A61K 9/06* | (2006.01) |
| *A61K 45/06* | (2006.01) |
| *A45D 40/04* | (2006.01) |

(52) U.S. Cl.
CPC ............ *A61K 9/0014* (2013.01); *A45D 40/04* (2013.01); *A61K 8/0229* (2013.01); *A61K 8/96* (2013.01); *A61K 9/06* (2013.01); *A61K 45/06* (2013.01); *A61Q 15/00* (2013.01); *A61K 2800/87* (2013.01)

(58) Field of Classification Search
CPC combination set(s) only.
See application file for complete search history.

(56) References Cited

U.S. PATENT DOCUMENTS

| | | | |
|---|---|---|---|
| 8,187,578 B2 | 5/2012 | Walling et al. | |
| 2003/0171702 A1* | 9/2003 | Thompson | A45D 33/02 601/72 |
| 2005/0142085 A1 | 6/2005 | Takeuchi et al. | |
| 2006/0239939 A1 | 10/2006 | Hiramoto et al. | |

* cited by examiner

*Primary Examiner* — David Walczak (57) ABSTRACT

A line of stick-style deodorants and antiperspirants that, in addition to their normal use, are infused with a vast array of vitamins and minerals that can be absorbed into the body upon application to provide consumers with a unique, easy, and hassle-free means of achieving optimal daily vitamin intake.

5 Claims, 4 Drawing Sheets

DEODORANT HEALTH SYSTEMS

CROSS-REFERENCE TO RELATED APPLICATION

The present application is related to and claims priority from prior provisional application Ser. No. 61/930,067, filed Jan. 22, 2014 which application is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71 (d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of deodorants and antiperspirants and more specifically relates to a specialty deodorant inclusive of a topical composition suitable to be applied to a body to decrease body odor and to achieve added health benefits.

2. Description of the Related Art

According to the Institute of Medicine of the National Academies, vitamins and minerals are substances the body needs in small amounts for normal growth, function, and health. In addition to facilitating normal body functions, mental alertness, and resistance to infection, vitamins enable the body to process proteins, carbohydrates, and fats. Many vitamins also help to produce blood cells, hormones, genetic material, and chemicals in the nervous system. Unlike carbohydrates, proteins, and fats, vitamins and minerals do not provide calories; however, they assist the body in releasing and using calories from food. These micronutrients are not naturally created by the body, so they must be taken from food or, in many cases, from supplements. Offered in pill form, vitamin and mineral supplements are taken by millions of Americans, both children and adults, every day. Many times these may be forgotten in the everyday rush.

Whether vitamin A for healthy vision, bone growth, and reproduction; calcium for strong teeth and bones and for muscle and nerve function; or vitamin C to maintain skin integrity and to fortify the immune system, many medicine chests and kitchen cabinets are filled to bursting with bottles of vitamin supplements. While vitamins are important for optimal health, many consumers would readily attest that it can be a daunting challenge to keep up with such a plethora of supplements while also having to remember the recommended daily dosage of each one, especially on hectic and busy days. In addition, these pills tend to be quite large and hard to swallow, while also producing an unpleasant taste. For these reasons, many health conscious consumers may inadvertently forget to take a needed vitamin or worse, decide the effort is too overwhelming or unappealing and opt to not take vitamins at all.

Individuals often wear deodorant such that offensive odors are minimized and controlled or masked. Deodorants are not multi-functional in conventional offerings.

Various attempts have been made to solve problems found in deodorant compositions art. Among these are found in: U.S. Pat. No. 8,187,578 to David William Walling et al; U.S. Publication No. 2005/0142085 to Katsuhiko Takeuchi et al; and U.S. Publication No. 2006/0239939 to Tadahiro Hiramoto et al. This prior art is representative of deodorant and antiperspirant compositions. None of the above inventions and patents, taken either singly or in combination, is seen to describe the invention as claimed.

Ideally, a topical composition applied to a body to decrease body odor system while introducing the body to needed health promoters should be user-friendly and safe in-use and, yet may operate reliably and be manufactured at a modest expense. Thus, a need exists for a topical composition applied to a body to decrease body odor system infused with at least one daily supplement that is absorbed into the body upon application providing the user with a convenient means to achieve optimal daily supplement intake while applying the topical composition in a form of deodorant and to avoid the above mentioned problems.

BRIEF SUMMARY OF THE INVENTION

Ideally, a topical composition applied to a body (simultaneously with deodorant) to decrease body odor should be user-friendly and safe in-use and, yet may operate reliably and be manufactured at a modest expense. Thus, a need exists for a topical composition applied to a body to decrease body odor system infused with at least one daily supplement that is absorbed into the body upon application provides the user with a convenient means to achieve optimal daily supplement intake while applying the topical composition in a form of specialty deodorant.

A topical composition applied to a body to decrease body odor system is disclosed herein in a preferred embodiment comprising: a deodorant composition assembly having a semi-solid composition for neutralizing body odor; and at least one added said supplement including vitamins of vitamin A, vitamin C, vitamin D3, vitamin E, thiamin B1, riboflavin, niacin B3, vitamin B6, folic acid, vitamin B12, biotin, pantothenic acid, inositol, choline, and carotenoid mix, and antioxidants of CoQ10, pyrroloquinoline quinone, resveratrol, astrazanthin, ascorbate, and potassium iodide thereby forming a multivitamin complex. The semi-solid composition comprises the deodorant composition assembly.

The deodorant composition assembly is structured and arranged to be applied to aid the body to prevent body odor caused by bacterial breakdown of perspiration of the body. The deodorant composition assembly is infused with the at least one daily supplement that is absorbed into the body upon application to realize increased health benefits.

The supplement comprising the vitamins of vitamin A, vitamin C, vitamin D3, vitamin E, thiamin B1, riboflavin, niacin B3, vitamin B6, folic acid, vitamin B12, biotin, pantothenic acid, inositol, choline, and carotenoid mix, and antioxidants of CoQ10, pyrroloquinoline quinone, resveratrol, astrazanthin, ascorbate, and potassium iodide thereby form a multivitamin complex to comprise at least one included daily supplement admixture of topical composition for achieving optimal vitamin and dietary mineral levels.

The supplement is added to the semi-solid composition so as to provide a semi-solid deodorant (mixed during manufacture) which is applied to a body region to both deodorize and infuse healthy vitamins, minerals, and key nutrients consumed for daily use. The deodorant composition assembly provides the user with a convenient mean to achieve optimal daily supplement intake while applying the semi-solid composition in a form of deodorant; serving at least a dual purpose via a convenient means.

A method for manufacturing a host deodorant stick having at least one supplement system is disclosed in a preferred embodiment comprising the steps of: mixing ingredients for a deodorant stick; admixing a solution of healthy vitamins, minerals, and key nutrients in with the ingredients for a deodorant stick; solidifying mixture; and forming said mixture for use as a semi-solid composition suitable to achieve through use an optimal daily supplement intake while applying the semi-solid composition in a form of deodorant to create a healthful effect.

The present invention holds significant improvements and serves as a topical composition applied to a body to decrease body odor system and to realize healthful effect(s). For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention topical composition applied to a body to decrease body odor system (entitled Deodorant Health Systems) constructed and operative according to the teachings of the present invention.

The various embodiments of the present invention will hereinafter be described in conjunction with the appended drawings, wherein like designations denote like elements.

DETAILED DESCRIPTION

As discussed above, embodiments of the present invention relate to an apparel protecting knee pads device and more particularly to a topical composition applied to a body to decrease body odor system (entitled Deodorant Heath Systems) infused with at least one daily supplement that is absorbed into the body upon application providing the user with a convenient means to achieve optimal daily supplement intake while applying the topical composition in a form of deodorant.

Generally speaking, Deodorant Health Systems, also referred to herein as topical composition applied to a body to decrease body odor system and a host deodorant stick having at least one supplement system comprises a specially designed line of stick-style deodorants and antiperspirants that, in addition to their normal use, may be infused with a vast array of vitamins and minerals that may be absorbed into the body upon application. In this manner, one preferably is able to fight perspiration and odor while delivering a time-release dose of necessary vitamins and minerals through the skin into the bloodstream, all at the same time. Use of Deodorant Health may enable one to fight perspiration and odor while delivering a time-release dose of necessary vitamins and minerals through the skin into the bloodstream, all at the same time such that application is convenient.

The deodorant itself may be offered in the popular stick variety, or a compact, oval shaped powder bar or gel that is dispensed from its container via an internal plunger mechanism that raises the substance to the top surface for application. The odor/perspiration fighting ingredients of Deodorant Health may be comprised of those found in common varieties, with formulas and fragrances appropriate for men, women, and even children. Yet, it is the incorporation of vitamins and minerals into the product that sets it apart from standard deodorants. The adult version of Deodorant Health may contain the recommended daily dosage of all vitamins from A to Zinc, while the children's version may feature the ones they need most, which are A, C, and D.

Variations on the Deodorant Health concept that may facilitate time-release dispensation of other specific nutrients and medicinals may include but are not limited to testosterone for men, iron for women, pre-workout supplements, energy boosts, and even pain relievers. These are disclosed as exemplary means; it should be appreciated that there are many other ingredients that may be included in the deodorant formulation and that the exemplary means are not intended to be limiting in any of the scope of the present invention.

Distributing nutrients through the skin, this product preferably eliminates the need to purchase and keep track of a vast collection of all necessary vitamins. Additionally, consumers may avoid the hard-to-swallow, unpleasant tasting vitamins that are orally ingested. As one's hygienic ritual is essentially second nature, users may never forget their needed vitamins. Two fully functional products in one, the convenience offered by Deodorant Health Systems preferably appeals to virtually any adult, and even children.

Figure 1:
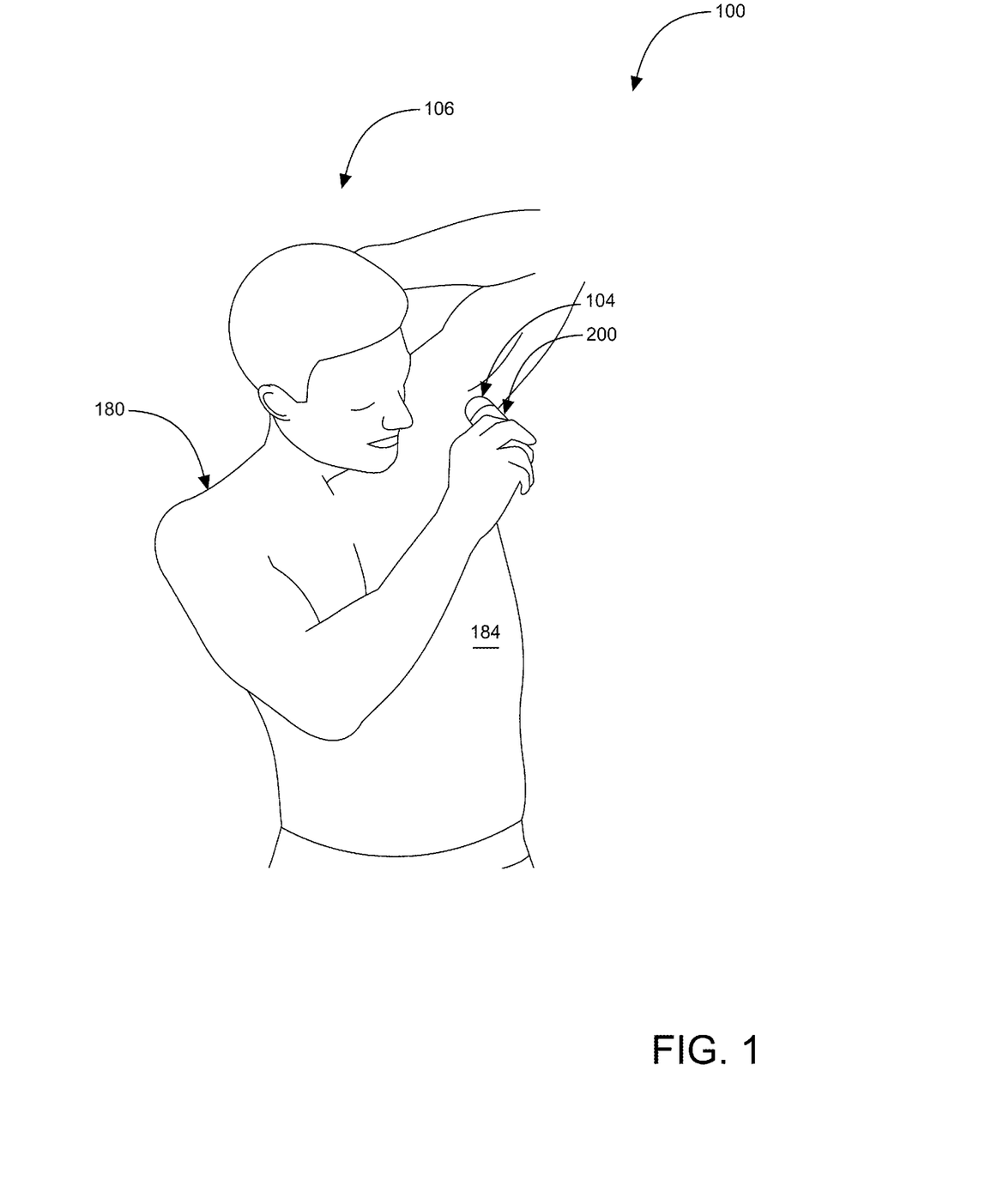
FIG. 1 shows a front perspective view illustrating a topical composition applied to a body to decrease body odor system in an 'in-use' condition according to an embodiment of the present invention.
Figure 2:
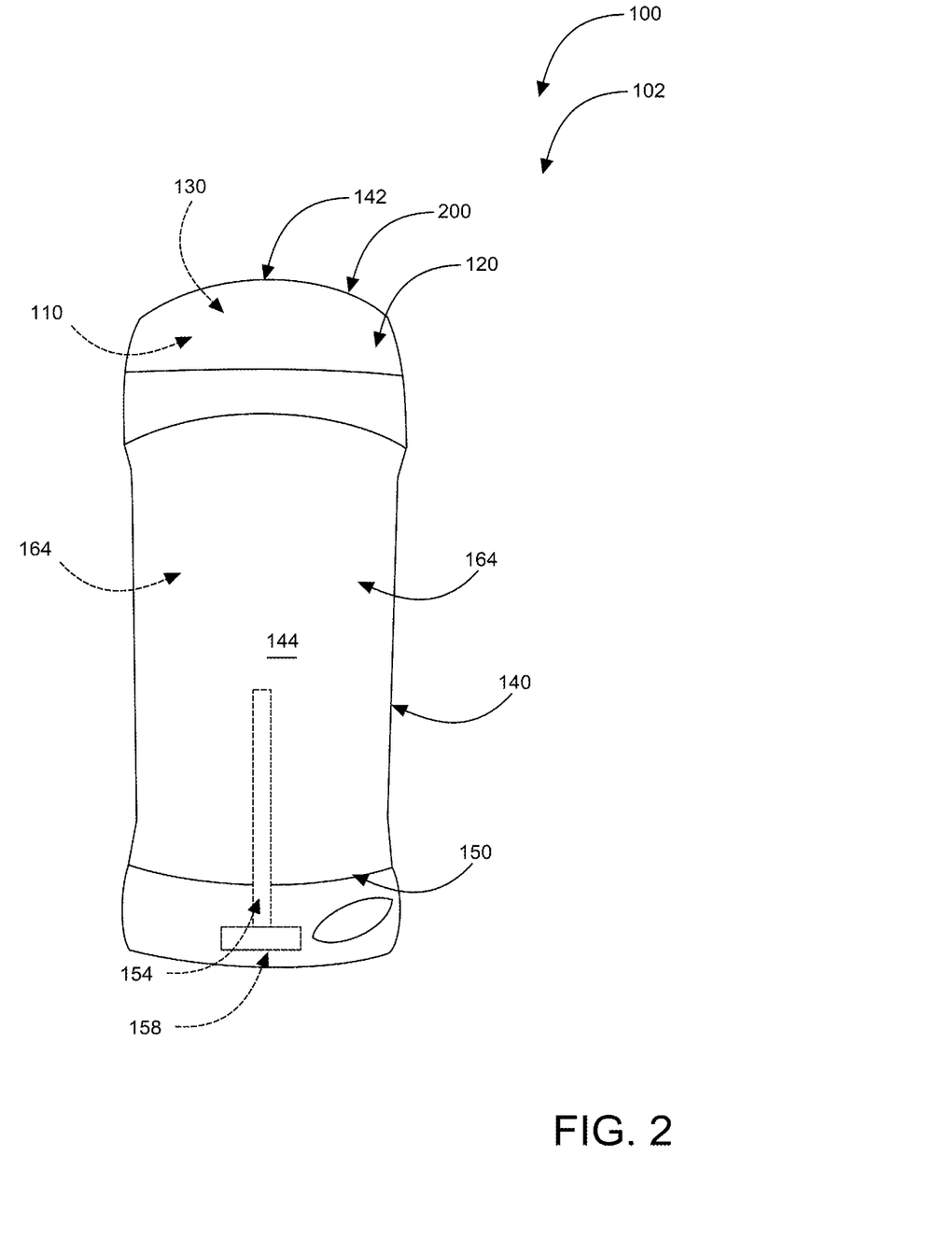
FIG. 2 shows a front perspective view illustrating a topical composition assembly of the topical composition applied to a body to decrease body odor system according to an embodiment of the present invention.
Figure 3:
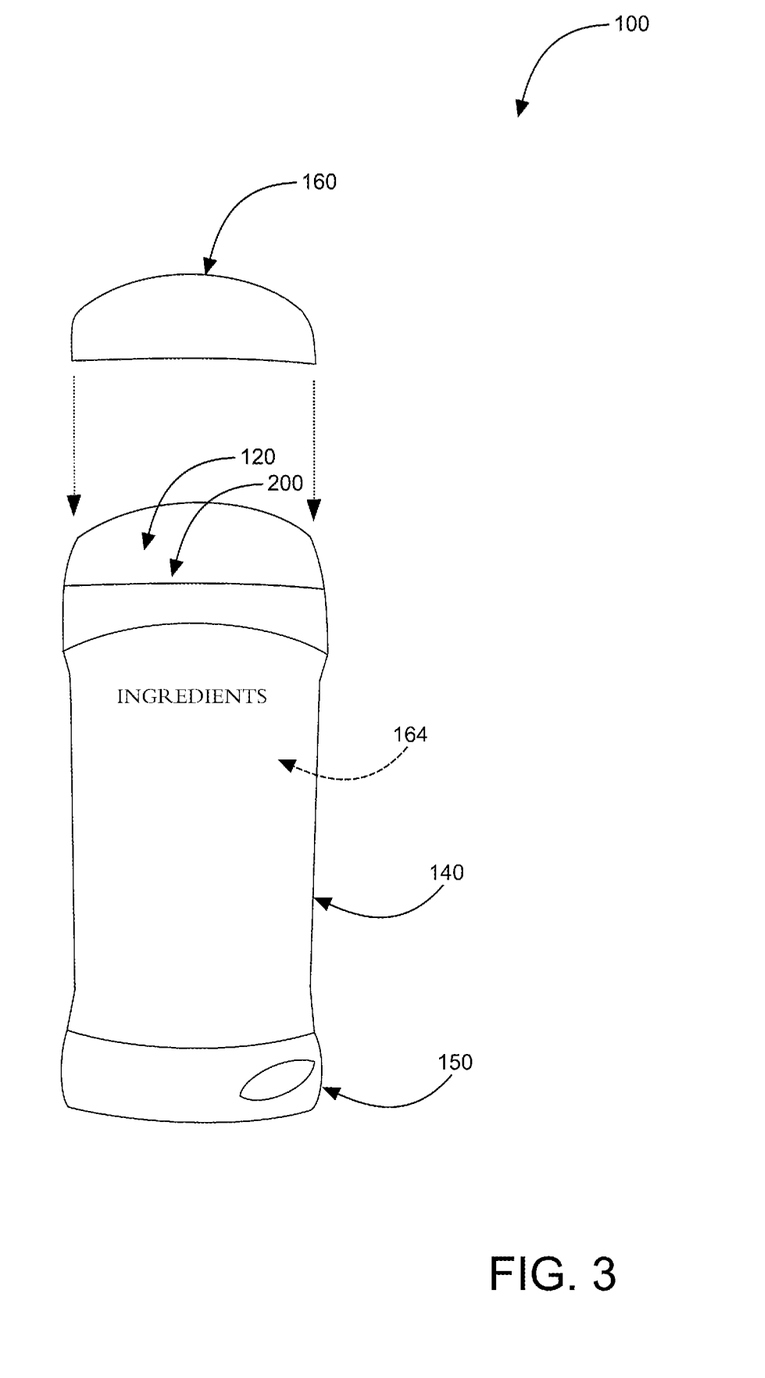
FIG. 3 is a perspective view illustrating topical composition assembly of the topical composition applied to a body to decrease body odor system according to an embodiment of the present invention.

Referring now to the drawings by numerals of reference there is shown in FIGS. 1-3 perspective views illustrating topical composition assembly 102 of topical composition applied to a body to decrease body odor system 100 according to an embodiment of the present invention.

Topical composition applied to a body to decrease body odor system 100 comprises: topical composition assembly 102 having topical composition 110 including semi-solid composition 120 for neutralizing body odor, at least one included daily supplement 130; and container 140 for storing topical composition 110 having peripheral side wall 144, base 150 having at least one plunger mechanism 154, and roll wheel 158, open top 160 for exposing topical composition 110, and interior volume 164 for storing topical composition 110. Topical composition applied to body to decrease body odor system 100 comprises topical composition assembly 102. Topical composition 110 and container 140 comprise topical composition assembly 102. Other dispensing means may be used.

Peripheral side wall 144; base 150; open top 160; and interior volume 164 define container 140 for storing topical composition 110. Topical composition 110 is dispensed from container 140 when roll-wheel 158 is preferably turned in a clock-wise position via thereby activating internal plunger mechanism 154 which raises topical composition 110 out of the open top of the container for application when to body region 184 of user 180 as shown in FIG. 1. Topical composition 110 is structured and arranged to be applied to body 184 to prevent body odor caused by bacterial breakdown of perspiration of body 184.

Topical composition 102 is infused with at least one daily supplement 130 that is absorbed into body 184 of user 180 upon application as shown in in-use condition 106 of FIG. 1. Topical composition assembly 102 provides user 180 with a convenient means to achieve optimal daily supplement intake while applying topical composition 110 in a form of deodorant 200 as shown in FIG. 2 or antiperspirant gel as shown in FIG. 3. Topical composition 110 comprises deodorant stick 104 as shown in FIGS. 1 and 2. Topical composition 110 may also comprise antiperspirant gel 300 which controls both body odor and sweat.

Supplement 130 may comprises vitamin B-12, vitamin B-9, vitamin B-3, vitamin E, vitamin B-5, vitamin B-6, vitamin B-2, vitamin B-1, vitamin A, vitamin K, and vitamin D thereby forming a B-12 Mega+10 complex to comprise at least one included daily supplement admixture of topical composition 110. The B-12 Mega+10 complex supplement comprises approximately 5,000 mcg of vitamin B-12, approximately 500 mcg of vitamin B-9, approximately 15 mg of vitamin B-3, approximately 15 mg of vitamin E, approximately 10 mg of vitamin B-5, approximately 3 mg of vitamin B-6, approximately 2 mg of vitamin B-2, approximately 2 mg of vitamin B-1, approximately 1 mg of vitamin A, approximately 150 mcg of vitamin K, and approximately 125 mcg of vitamin D.

The B-12 Complex may also be in the form of a B-12 Energy Complex supplement in alternate embodiments replacing the B-12 Mega+10. The B-12 Complex comprises approximately 1,000 mcg of vitamin B-12, approximately 400 mcg of vitamin B-9, approximately 19 mg of vitamin B-3, approximately 10 mg of vitamin E, approximately 5 mg of vitamin B-5, approximately 2 mg of vitamin B-6, approximately 1.7 mg of vitamin B-2, approximately 1.5 mg of vitamin B-1, approximately 1 mg of vitamin A, approximately 80 mcg of vitamin K, and approximately 5 mcg of vitamin D thereby forming a B-12 Energy Complex.

The B-12 Complex may also be in the form of a highest dose B-complex supplement available in a transdermal in alternate embodiments replacing the B-12 Mega+10. The highest dose B-complex supplement available in a transdermal complex comprises vitamin B-12, vitamin B-9, vitamin B-6, vitamin B-5, vitamin B-3, vitamin B-2, vitamin B-1, Biotin, and CitiCholine thereby forming the highest dose B-complex supplement available in a transdermal in.

The B-12 Complex may also be in the form of a B-12 Mega supplement in alternate embodiments replacing the B-12 Mega+10. The B-12 Mega Complex comprises approximately 5,000 mcg vitamin B-12 thereby forming the B-12 Mega supplement.

Supplement 130 may also comprises androstanetrione, l-arginine, stinging nettle root, cayenne, mulra puama, orchic substance, oyster meat, tribulus, zinc, sarsaparilla, astragaius, licorice root, pumpkin seed, boron, pygueum, maca, honey goat weed, oatstraw, catuaba, and d-aspartic acid thereby forming a natural testosterone booster complex to comprise at least one included daily supplement admixture of topical composition 110.

The natural testosterone booster comprises approximately 21 mg androstanetrione, approximately 1 mg L-arginine, approximately 14.50 mg stinging nettle root, approximately 1 mg cayenne, approximately 1 mg mulra puama, approximately 1 mg orchic substance, approximately 1 mg oyster meat, approximately 1 mg tribulus, zinc, approximately 1 mg sarsaparilla, approximately 1 mg astragaius, approximately 1 mg licorice root, approximately 1 mg pumpkin seed, approximately 1 mg boron, approximately 1 mg pygueum, approximately 1 mg maca, approximately 1 mg honey goat weed, approximately 1 mg oatstraw, approximately 1 mg catuaba, and approximately 22 mg D-aspartic acid thereby forming the natural testosterone booster.

The Natural Testosterone Booster may also be in the form of a New Testosterone/1000 supplement in alternate embodiments replacing the Natural Testosterone Booster. The New Testosterone/1000 comprises approximately 21 mg androstenetrione, approximately 22 mg D-aspartic acid, approximately 14.5 mg stinging nettle root, approximately 6.5 mg muira pauma, approximately 1 mg tribulus, approximately 1 mg zinc, approximately 1 mg boron, approximately 1 mg maca, approximately 1 mg homey goat weed, approximately 3 mg furostanolic saponins from fenugreek, and approximately 3 mg forskolin from *coleus forskohlii* thereby forming the New Testosterone/1000.

Supplement 130 may also comprise glutathione, ascorbic acid, anthocyanin, alpha-tocopherol, and xanthone thereby forming an anti-oxidant gluthione complex to comprise said at least one included daily supplement admixture of topical composition 110. The anti-oxidant glutathione comprises approximately 5 mg glutathione from avocado, approximately 5 mg ascorbic acid from bananas, approximately 10 mg anthocyanin from acai berry, approximately 10 mg alpha-tocopherol from acai berry, and approximately 20 mg xanthone from manggis.

Supplement 130 may also comprise glucosamine sulfate, chondroitin, catyimeristoleate, and thiamine HCL thereby forming a glucosamine complex to comprise said at least one included daily supplement admixture of topical composition 110. The glucosamine complex comprises approximately 23 mg glucosamine sulfate, approximately 4 mg chondroitin, approximately 4 mg catyimeristoleate, and approximately 2 mg thiamine HCL.

Supplement 130 may also comprises garcinia cambogia, 7-keto DHEA, tyr-somatostatin, R alpha lipoic acid, hoodia, yohimbine, and hordenine thereby forming a fat burning weight loss complex to comprise at least one included daily supplement admixture of topical composition 110. The fat burning weight loss complex comprises in a preferred embodiment approximately 10 mg garcinia cambogia, approximately 20 mg 7-keto DHEA, approximately 5 mg Tyr-Somatostatin, approximately 4 mg R alpha lipoic acid, approximately 11 mg hoodia, approximately 10 mg yohimbine, and approximately 15 mg hordenine.

In an alternate embodiment the fat burning weight loss complex may be in the form of a slimming complex with hoodie and green tea comprising approximately 10 mg hoodia gordonil, approximately 0.75 mg citrus aurantium, approximately 24 mg guarana, and approximately 10 mg premium green tea extract.

Supplement 130 may also comprises Omega-3 and coenzyme Q10 thereby forming an Omega 3+Coq10 complex to comprise at least one included daily supplement admixture of topical composition 110. The Omega 3+CoQ10 complex comprises approximately 25 mg Omega-3 and approximately 24 mg Coenzyme Q10.

Supplement 130 may also comprises calcium, vitamin D3, phosphorus, magnesium, and protein thereby forming a vitamin D3 Calcium complex to comprise said at least one included daily supplement admixture of topical composition 110. The vitamin D3 Calcium complex comprises approximately 32.6175 mg calcium, approximately 0.032225 mg vitamin D3, approximately 18.305 mg phosphorus, approximately 9.78 mg magnesium, and approximately 18.305 mg protein.

Supplement 130 may also comprises melatonin and gamma-aminobutyric acid thereby forming a melatonin and insomnia complex to comprise said at least one included daily supplement admixture of topical composition 110. The melatonin and insomnia complex comprises approximately 5.0 mg melatonin and approximately 4.0 mg gamma-aminobutyric acid.

Supplement 130 may also comprises foti, *ginseng*, Siberian *ginseng*, damiana, gotu-kola, saw palmetto, and yohimba thereby forming a male potency booster to comprise the at least one included daily supplement admixture of topical composition 110. The male potency booster complex comprises approximately 1.50 mg foti, approximately 1.25 mg *ginseng*, approximately 1.50 mg Siberian *ginseng*, approximately 2.50 mg damiana, approximately 1.50 mg gotu-kola, approximately 1.70 mg saw palmetto, and approximately 0.05 mg yohimba.

In an alternate embodiment the male potency booster complex may be in the form of a male sexual performance enhancement complex comprising 12.5 mg butea superba, approximately 42.5 mg ginsenosi de Rg1, approximately 15 mg icarlin, and approximately 2.5 mg yohimbine.

Supplement 130 may also comprises L-Arginine, citrulline, L-Lysine, and ginko biloba thereby forming a nitric oxide booster complex to comprise at least one included daily supplement admixture of topical composition 110. The nitric oxide booster complex supplement comprises approximately 50 mg L-Arginine, approximately 5 mg citrulline, approximately 10 mg L-Lysine, and approximately 10 mg ginko biloba.

Supplement 130 may also comprises vitamins of vitamin A, vitamin C, vitamin D3, vitamin E, thiamin B1, riboflavin, niacin B3, vitamin B6, folic acid, vitamin B12, biotin, pantothenic acid, inositol, choline, and carotenoid mix, and antioxidants of CoQ10, pyrroloquinoline quinone, resveratrol, astrazanthin, ascorbate, and potassium iodide thereby forming a multivitamin complex to comprise said at least one included daily supplement admixture of topical composition 110. A multivitamin complex comprising vitamins of approximately 250 mcg vitamin A, approximately 10 mg vitamin C, approximately 60 mcg vitamin D3, approximately 10 mg vitamin E, approximately 5 mg thiamin B1, approximately 5 mg riboflavin, approximately 5 mg niacin B3, approximately 5 mg vitamin B6, approximately 250 mcg folic acid, approximately 100 mcg vitamin B12, approximately 150 mcg biotin, approximately 2.5 mg pantothenic acid, approximately 2.5 mg inositol, approximately 1 mg choline, and approximately 200 mcg carotenoid mix, and antioxidants of approximately 7 mg CoQ10, approximately 2 mg pyrroloquinoline quinone, approximately 5 mg resveratrol, approximately 3 mg astrazanthin, approximately 10 mg ascorbate, and 1 mg potassium iodide.

Supplement 130 may also comprise *perilla frutescens* extract standardized for 75 percent *perilla frutescens* thereby forming an allergy relief complex to comprise the at least one included daily supplement admixture of topical composition 110. The allergy relief complex comprises approximately 75 mg *perilla frutescens* extract standardized for 75 percent *perilla frutescens*.

Supplement 130 may also comprise GH produced by recombinant DNA technology in the form of somatropin and an amino acid appetite and weight control complex thereby forming an extra strength HGH complex to comprise the at least one included daily supplement admixture of topical composition 110. The extra strength HGH complex comprising approximately 22,500 ng GH produced by recombinant DNA technology in the form of somatropin and approximately 2,000 ng amino acid appetite and weight control complex.

In an alternate embodiment the extra strength HGH complex may be in the form of a HGH power complex comprising approximately 25 mg GH produced by recombinant DNA technology in the form of somatropin.

Supplement 130 may also comprise a transdermal nitro glycerin complex comprising approximately a range of 0.2 mg/h to 0.6 mg/h niro-gylcerin with a max dose of 15 mg consumed in a 24 hour period to comprise at least one included daily supplement admixture of topical composition 110.

Supplement 130 may also comprise lysine, leucine, phenylalanine, valine, isoleucine, methionine, threonine, tryptophan, and tyrosine thereby forming an essential amino acid complex to comprise the at least one included daily supplement admixture of topical composition 110. The essential amino acid complex comprises approximately 12 mg lysine, approximately 11 mg leucine, approximately 10 mg phenylalanine, approximately 10 mg valine, approximately 8 mg isoleucine, approximately 8 mg methionine, approximately 8 mg threonine, approximately 3 mg tryptophan, and approximately 2 mg tyrosine thereby forming a useful healthful mixture.

Supplement 130 may also comprise energy complex comprises approximately 26 mg guarana, approximately 10 mg 5-HTP, approximately 3 mg zinc pyruvate, approximately 2 mg yerba mate, approximately 1 mg flax seed oil, approximately 1 mg L-carnitine, approximately 1 mg lecithin, and approximately 1 mg zinc citrate thereby forming an energy complex.

Figure 4:
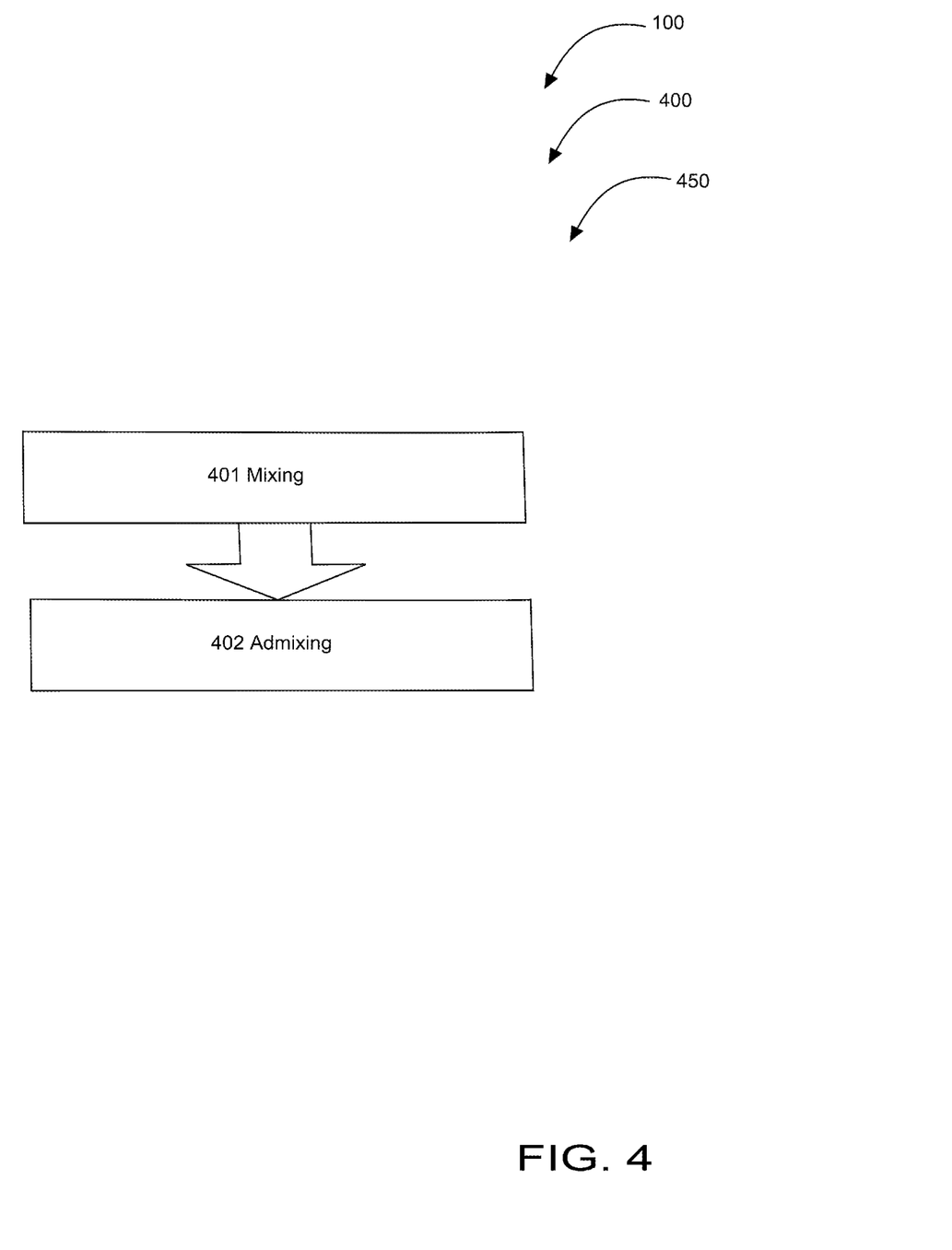
FIG. 4 is a flowchart illustrating a method of manufacturing for the host deodorant stick having at least one supplement system according to an embodiment of the present invention of FIGS. 1-3.

Referring now to FIG. 4, flowchart 450 illustrating method of manufacturing 400 for topical composition applied to a body to decrease body odor system (host deodorant stick having at least one supplement system) 100 according to an embodiment of the present invention of FIGS. 1-3.

A method for manufacturing a host deodorant stick having at least one supplement system 100 comprises the steps of: step one 401 mixing ingredients for deodorant stick 104; step two 402 admixing a solution of healthy vitamins, minerals, and key nutrients in with ingredients for deodorant stick 104; solidifying mixture; and forming the mixture for use as semi-solid composition 120 suitable to achieve through use an optimal daily supplement intake while applying semi-solid composition 120 in a form of deodorant to create a healthful effect.

It should be noted that the steps described in the method of use can be carried out in many different orders according to user preference. The use of "step of" should not be interpreted as "step for", in the claims herein and is not intended to invoke the provisions of 35 U.S.C. §112, ¶ 6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A topical composition applied to a body to decrease body odor system comprising:
   a topical composition assembly having,
      a topical composition including,
         a semi-solid composition for neutralizing body odor; and
         at least one included daily supplement; and
      a container for storing said topical composition having,
         a peripheral side wall;
         a base having,
            at least one internal plunger mechanism, and
            a roll wheel;
         an open top for exposing said topical composition; and
         an interior volume for storing said topical composition;
   wherein said topical composition applied to a body to decrease body odor system comprises said topical composition assembly;
   wherein said topical composition and said container comprise said topical composition assembly;
   wherein said peripheral side wall; said base; said open top; and said interior volume define said container for storing said topical composition;
   wherein said topical composition is dispensed from said container when said roll-wheel is turned in a clock-wise position thereby activating said internal plunger mechanism which raises an upper surface of said topical composition out of said open top of said container for application when to a body region of a user;
   wherein said topical composition is structured and arranged to be applied to said body to prevent body odor caused by bacterial breakdown of perspiration of said body;
   wherein said topical composition is infused with said at least one daily supplement that is absorbed into said body upon application wherein said supplement comprises garcinia cambogia, 7-keto DHEA, tyr-somatostatin, R alpha lipoic acid, hoodia, yohimbine and hordenine thereby forming a fat-burning weight loss complex; and
   wherein said topical composition assembly provides said user with a convenient means to achieve optimal daily supplement intake while applying said topical composition in a form of deodorant.

2. The topical composition applied to a body to decrease body odor system of claim 1 wherein said topical composition comprises a deodorant stick.

3. The topical composition applied to a body to decrease body odor system of claim 1 wherein said topical composition comprises an antiperspirant gel which controls both said body odor and sweat.

4. A topical composition applied to a body to decrease body odor system comprising: a topical composition assembly having a topical composition including a semi-solid composition for neutralizing body odor and at least one included daily supplement and a container for storing said topical composition having a peripheral side wall, a base having at least one internal plunger mechanism and a roll wheel, an open top for exposing said topical composition and an interior volume for storing said topical composition, wherein said topical composition applied to a body to decrease body odor system comprises said topical composition assembly, wherein said topical composition and said container and said container comprise said topical composition assembly, wherein said peripheral side wall, said base, said open top and said interior volume define said container for storing said topical composition, wherein said topical composition is dispensed from said container when said roll wheel is turned in a clock-wise position thereby activating said internal plunger mechanism which raises an upper surface of said topical composition out of said open top of said container for application to a body region of a user, wherein said topical composition is structured and arranged to be applied to said body to prevent body odor caused by bacterial breakdown of perspiration of said body, wherein said topical composition is infused with said at least one daily supplement that is absorbed into said body upon application where said supplement comprises GH produced by recombinant DNA technology in the form of somatropin and an amino acid appetite and weight control complex thereby forming an extra strength HGH complex to comprise said at least one included daily supplement admixture of said topical composition and wherein said topical composition assembly provides said user with a convenient means to achieve optimal daily supplement intake while applying said topical composition in a form of deodorant.

5. A topical composition applied to a body to decrease body odor system comprising: a topical composition assembly having a topical composition including a semi-solid composition for neutralizing body odor and at least one included daily supplement and a container for storing said topical composition having a peripheral side wall, a base having at least one internal plunger mechanism and a roll wheel, an open top for exposing said topical composition and an interior volume for storing said topical composition, wherein said topical composition applied to a body to decrease body odor system comprises said topical composition assembly, wherein said topical composition and said container and said container comprise said topical composition assembly, wherein said peripheral side wall, said base, said open top and said interior volume define said container for storing said topical composition, wherein said topical composition is dispensed from said container when said roll wheel is turned in a clock-wise position thereby activating said internal plunger mechanism which raises an upper surface of said topical composition out of said open top of said container for application to a body region of a user, wherein said topical composition is structured and arranged to be applied to said body to prevent body odor caused by bacterial breakdown of perspiration of said body, wherein said topical composition is infused with said at least one daily supplement that is absorbed into said body upon application where said supplement comprises *perilla frutescens* extract standardized for 75 percent *perilla frutescens* thereby forming an allergy relief complex to comprise said at least one included daily supplement admixture of said topical composition and wherein said topical composition assembly provides said user with a convenient means to achieve optimal daily supplement intake while applying said topical composition in a form of deodorant.

\* \* \* \* \*